July 7, 1964 J. M. GARABEDIAN Plant Pat. 2,420
PLUM TREE
Filed July 5, 1963
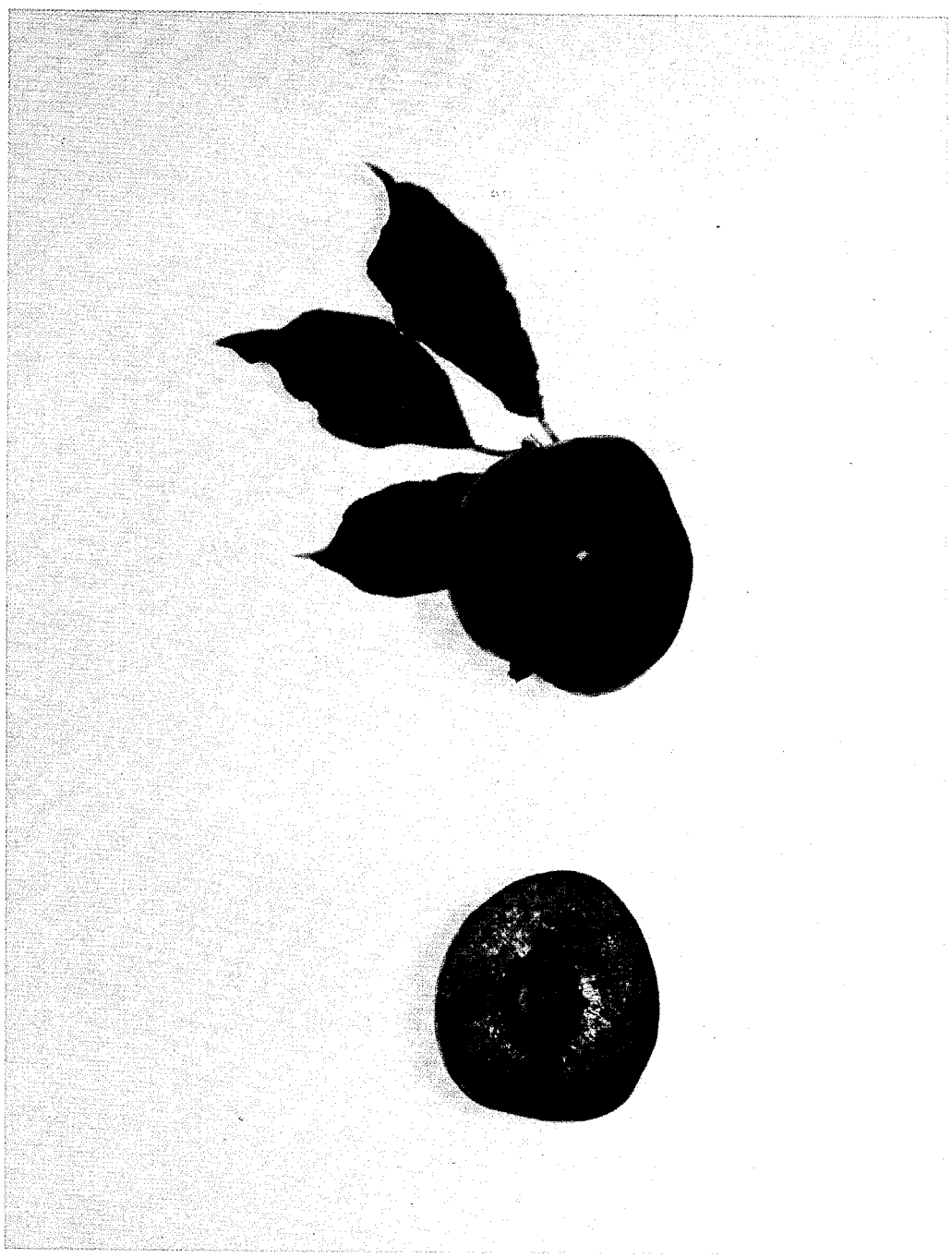
INVENTOR
John M. Garabedian
Webster & Webster
ATTYS.

United States Patent Office

Plant Pat. 2,420
Patented July 7, 1964

2,420
PLUM TREE

John M. Garabedian, Fresno, Calif., assignor to Peach & Willow Farms, Fresno, Calif., a corporation of California Filed July 5, 1963, Ser. No. 293,219
1 Claim. (Cl. Plt.—38)

This invention relates to a new and distinct variety of plum tree originated by me in an experimental nursery at a ranch located near Fresno, county of Fresno, California; the variety being an open pollenated seedling of the Queen Ann plum (unpatented).

Upon recognition by me of the novel and distinctive characteristics (as hereinafter described) of the original tree of the present variety, I selected it for further testing and observation; this including asexual reproduction of the variety and which was accomplished, under my control and direction, by budding on mature trees in an experimental orchard on the ranch located as aforesaid. Under careful observation, I ascertained that such asexual reproductions ran true to the original tree in all respects, and that the variety had substantial commercial potential.

The present variety of plum tree is particularly characterized, as to novelty:

By flowering approximately five days later than the Santa Rosa plum (unpatented);

By the bearing of large clingstone fruit having very firm flesh which is bright red when eating ripe and which turns a darker red in the progression toward overripe;

By black skin covered with a blue-gray blush; and

By fruit that hangs well on the tree; i.e. remains thereon in excellent market condition for a relatively long time whereby the harvest period may extend over a span of at least five weeks.

In comparison to the Duarte plum (unpatented), the present variety matures about three weeks later, has much firmer flesh, and has a smooth black skin as distinguished from the mottled brownish-black skin color of said Duarte.

The drawing comprises an illustration, by photographic reproduction in color, of one fruit in elevation with leaves, and a half of another fruit cut to show the flesh and with the stone remaining in place.

Referring now more specifically to the pomological details of this new and distinct variety of plum tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Medium.
- *Growth.*—Upright.
- *Density.*—Dense.
- *Form.*—Vase shaped.
- *Hardiness.*—Hardy.
- *Production.*—Very productive.
- *Bearing.*—Regular bearer.

Trunk:
- *Form.*—Medium.
- *Texture.*—Medium.

Branches:
- *Form.*—Medium.
- *Texture.*—Medium.
- *Color.*—Brown.

Leaves:
- *Size.*—Medium. Average length—2½" to 4¼". Average width—1¼" to 1⅞".
- *Form.*—Oblong—ovate. Acutely pointed.
- *Thickness.*—Medium.
- *Color.*—Medium green.
- *Texture.*—Smooth.
- *Margin.*—Finely serrate.
- *Petiole.*—Medium length; medium thickness.
- *Glands.*—Average number—two to four. Small; globose. Green, with trace of yellow. Variably positioned on petiole and at base of blade.
- *Stipules.*—Wanting.

Flower buds:
- *Hardiness.*—Hardy.
- *Size.*—Small.
- *Length.*—Medium.
- *Form.*—Conic to pointed; free.
- *Surface.*—Glabrous.

Flowers:
- *Blooming period.*—About five days after the Santa Rosa plum. Medium, as compared to other varieties.
- *Size.*—Medium.
- *Color.*—White.
- *Anthers.*—Pink (6–J–9), shaded with yellow.

Fruit:
- *Maturity when described.*—Eating ripe.
- *Date of first picking.*—July 20, 1962.
- *Date of last picking.*—August 25, 1962.
- *Size.*—Uniform; large. Average diameter axially—2" to 2¾". Average transversely in suture plane—1¾" to 2½".
- *Form.*—Uniform; symmetrical. Some fruits slightly enlarged on one side of suture. Compressed somewhat on suture toward apex, with slight rounded point beyond apex.
- *Suture.*—Shallow. Extends from base to a little beyond pistil point, being slightly deeper at apex.
- *Ventral surface.*—Rounded. Some fruits tend to be slightly compressed on right of suture and to a point therebeyond.
- *Cavity.*—Elongated in suture plane with suture showing on both sides. Average depth—¼" to ⅜". Average breadth—½" to ⅝".
- *Base.*—Rounded.
- *Apex.*—Rounded to somewhat compressed, with a slight rounded point beyond apex.

Skin:
- *Thickness.*—Medium.
- *Texture.*—Tough.
- *Tenacity.*—Tenacious to flesh.
- *Tendency to crack.*—Very slight.
- *Color.*—Black with blue-gray bloom (44–A–5).

Flesh:
- *Color.*—Bright red (4–I–6) turning dark red (53–L–4) in the progression toward overripe.
- *Amygdalin.*—Wanting.
- *Texture.*—Crisp; meaty; very firm.
- *Fibers.*—Few; fine.
- *Ripens.*—Evenly.
- *Flavor.*—Slightly acid at early maturity.
- *Aroma.*—Distinct.
- *Eating quality.*—Excellent.

Stone:
- *Type.*—Clingstone. Adheres to flesh over entire surface along both dorsal and ventral edges. Short fibers.
- *Size.*—Small. Average length—¾" to 1". Average breadth—⅝" to ⅞". Average thickness—⅜" to ½".
- *Form.*—Oval.
- *Base.*—Straight.
- *Hilum.*—Narrow; small.
- *Apex.*—Rounded.
- *Sides.*—Equal.

*Surface.*—Regular; smooth.

*Ridges.*—Interrupted; ridged toward apex; slight ridges along ventral edge.

*Ventral edge.*—Very shallow.

*Dorsal edge.*—Very shallow, with narrow groove. Only present toward base and apex on some stones, rounded in center.

*Color.*—Brown (7–J–11).

*Tendency to split.*—Slight.

Use: Market; dessert.

Keeping quality: Excellent.

Shipping quality: Excellent.

The plum tree and its fruit herein described may vary in slight detail due to climatic and soil conditions under which the variety may be grown; the present description being of the variety as grown in the Central Valley of California.

The following is claimed:

A new and distinct variety of plum tree substantially as illustrated and described, characterized by flowering about five days after the Santa Rosa and by the regular and productive bearing of large clingstone fruit having very firm red flesh and black skin blushed blue-gray, the fruit hanging on the tree for a substantial period of time while remaining in excellent market condition; and further characterized in comparison to the Duarte by a harvest approximately three weeks later, by firmer flesh, and by smooth black skin as distinguished from the mottled brownish-black skin of said Duarte.

No references cited.